(12) United States Patent
Drenguis

(10) Patent No.: US 8,834,808 B2
(45) Date of Patent: Sep. 16, 2014

(54) DEVICE FOR STERILIZING CLOSURES FOR CONTAINERS

(75) Inventor: Alfred Drenguis, Börnsen (DE)

(73) Assignee: KHS GmbH, Dortmund (DE)

( * ) Notice: Subject to any disclaimer, the term of this patent is extended or adjusted under 35 U.S.C. 154(b) by 0 days.

(21) Appl. No.: 13/695,550

(22) PCT Filed: Mar. 24, 2011

(86) PCT No.: PCT/EP2011/001465
§ 371 (c)(1),
(2), (4) Date: Oct. 31, 2012

(87) PCT Pub. No.: WO2012/000573
PCT Pub. Date: Jan. 5, 2012

(65) Prior Publication Data
US 2013/0052089 A1    Feb. 28, 2013

(30) Foreign Application Priority Data
Jun. 29, 2010    (DE) .................. 10 2010 025 541

(51) Int. Cl.
| | | |
|---|---|---|
| A61L 2/00 | (2006.01) | |
| A61L 9/00 | (2006.01) | |
| B08B 3/00 | (2006.01) | |
| A61L 2/07 | (2006.01) | |
| A61L 2/22 | (2006.01) | |
| A61L 12/00 | (2006.01) | |
| B67C 7/00 | (2006.01) | |

(52) U.S. Cl.
CPC ... *A61L 2/00* (2013.01); *A61L 2/07* (2013.01); *A61L 2/22* (2013.01); *A61L 12/00* (2013.01); *B67C 7/00* (2013.01);
USPC .......... 422/292; 422/295; 422/297; 422/298; 422/300; 422/305; 422/307; 134/61; 134/84

(58) Field of Classification Search
CPC ............... A61L 2/00; A61L 2/07; A61L 2/22; A61L 12/00; B67C 7/00
USPC ......... 422/292, 295, 297–298, 300, 305, 307; 134/61, 84
See application file for complete search history.

(56) References Cited

U.S. PATENT DOCUMENTS

2011/0016829 A1    1/2011  Drenguis et al.

FOREIGN PATENT DOCUMENTS

| | | |
|---|---|---|
| DE | 10 2004 030 956 | 1/2006 |
| DE | 10 2008 007 428 | 8/2009 |

(Continued)

*Primary Examiner* — Monzer R Chorbaji
(74) *Attorney, Agent, or Firm* — Occhiuti & Rohlicek LLP

(57) ABSTRACT

An apparatus for sterilizing cap-like container closures includes a transport system for moving closures through treatment zones. The first zone preheats the closures, the second exposes them to a sterilizing agent, and the third activates or dries them. The first and third zones each have a rotor that circulates about a rotor axis thereof, and closure holders formed on a periphery thereof for moving closures through the first zone from a closure pickup disposed therein to a first closure delivery position, and through the third zone from a second closure delivery position disposed therein to a closure discharge. The second treatment zone is between the first and second closure delivery positions such that closures delivered to the first position, after passing the second zone and after exposure to the sterilizing agent, are passed on to a closure holder ready at the second position of the rotor in the third zone.

21 Claims, 6 Drawing Sheets

(56) References Cited

FOREIGN PATENT DOCUMENTS

| | | |
|---|---|---|
| DE | 10 2008 048 351 | 4/2010 |
| EP | 1 749 747 | 2/2007 |
| ES | EP 1 749 747 A1 * | 7/2007 ............. B65B 55/02 |
| JP | 2003-128023 | 5/2003 |
| WO | WO 00/46142 | 8/2000 |
| WO | WO 2010/031464 | 3/2010 |

* cited by examiner

DEVICE FOR STERILIZING CLOSURES FOR CONTAINERS

CROSS REFERENCE TO RELATED APPLICATION

This application is the national phase under 35 USC 371 of international application no. PCT/EP2011/001465, filed Mar. 24, 2011, which claims the benefit of the priority date of German application no. 10 2010 025 541.6, filed Jun. 29, 2010. The contents of the aforementioned applications are incorporated herein in their entirety.

FIELD OF DISCLOSURE

The invention relates to a device for sterilizing closures.

BACKGROUND

It is conventional and well-known, for example in plants in the drinks industry, to sterilize the closures used to close filled bottles or other containers, in particular cap-like closures such as screw closures, flat caps, crown corks etc., before use, i.e. before application to the container concerned, inter alia using sterilizing agents that consist of $H_2O_2$ vapor (vaporized aqueous hydrogen peroxide solution with sufficiently high concentration of $H_2O_2$) or a gaseous and/or vaporous carrier medium enriched with $H_2O_2$ vapor. To achieve an effective sterilization with high disinfection rate, before exposure to the sterilizing agent the closures are preheated for example to a temperature in the range between 50° C. and 85° C., and then after treatment or exposure to the gaseous and/or vaporous sterilizing agent, dried using a preferably heated sterile gaseous and/or vaporous medium, for example using preferably heated sterile air, so that the sterilized closures can then be used for closing containers or supplied to a closing machine for this.

SUMMARY

The object of the invention is to produce a device that allows a high performance (number of sterilized closures per time unit) with a high quality of sterilization or disinfection rate.

Particular advantages of the device according to the invention are, among others, that despite its high performance, the device can be produced very compactly with little construction space or volume, and that constant or reproducibly high disinfection rates are achieved on sterilization. The device according to the invention is suitable for closures of widely varying types, in particular also for cap-like closures such as screw closures, flat caps, crown corks etc.

Preferably, in the device according to the invention, the treatment zones there can be subjected to a slight positive pressure of a sterile gaseous and/or vaporous medium so that the penetration of ambient air and the germs carried with this into the treatment zones is effectively avoided, in particular also in the region of closure inlets and outlets.

Refinements, advantages and possible applications of the invention arise from the description below of embodiment examples and from the figures. All the features described and/or shown in the figures alone or in any combination are in principle the subject of the invention irrespective of their summary in the claims or back reference. The content of the claims is also made a constituent part of the description.

BRIEF DESCRIPTION OF THE FIGURES

The invention is described in more detail below with reference to the figures and one embodiment example in which.

DETAILED DESCRIPTION

Figure 1:
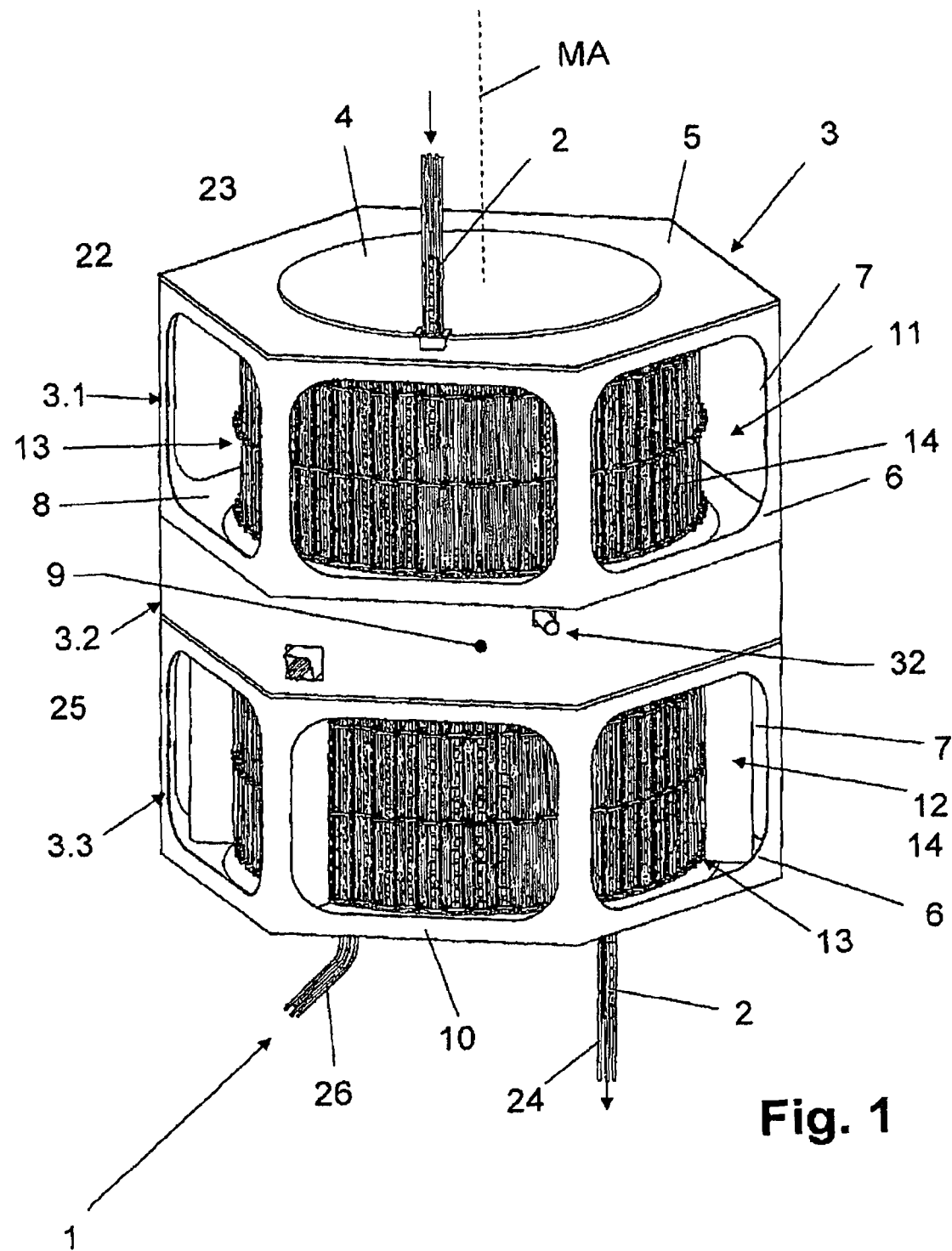
FIG. 1 shows, in perspective depiction and in various views, a device according to the invention for sterilizing closures intended for closing bottles or similar containers.
Figure 2:
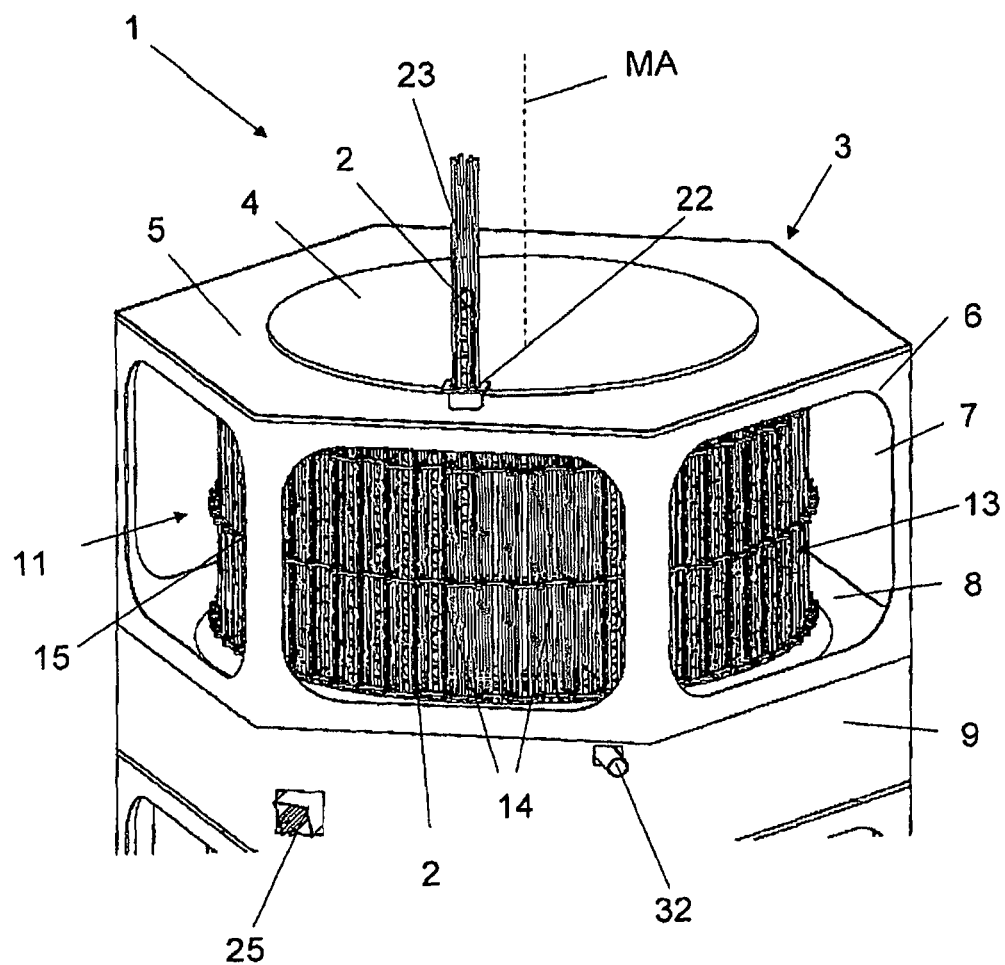
FIGS. 2 and 3 show, in enlarged perspective view, sections of the depiction in FIG. 1.
Figure 3:
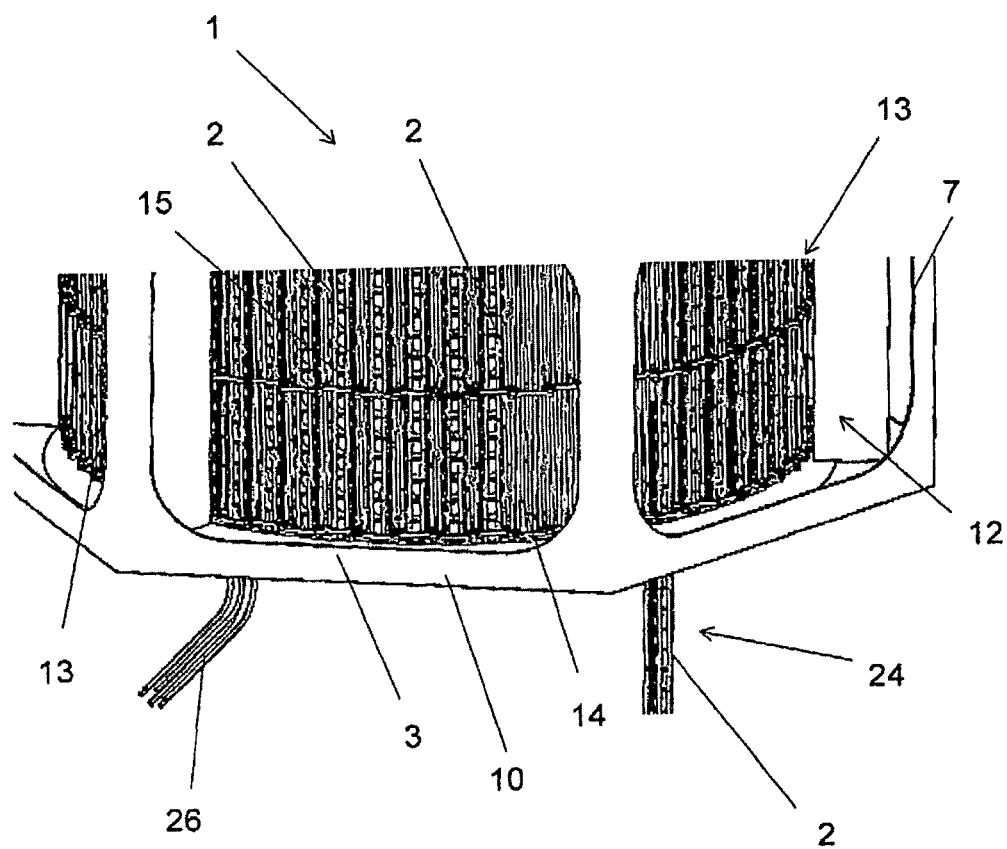
Figure 4:
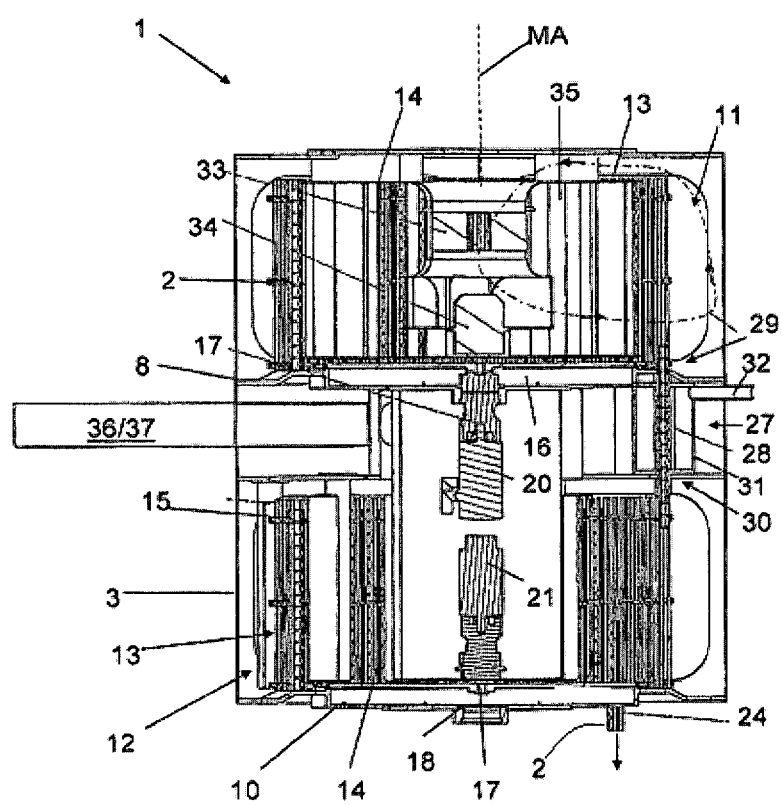
FIG. 4 is a simplified depiction of a vertical section of the device in FIG. 1.
Figure 5:
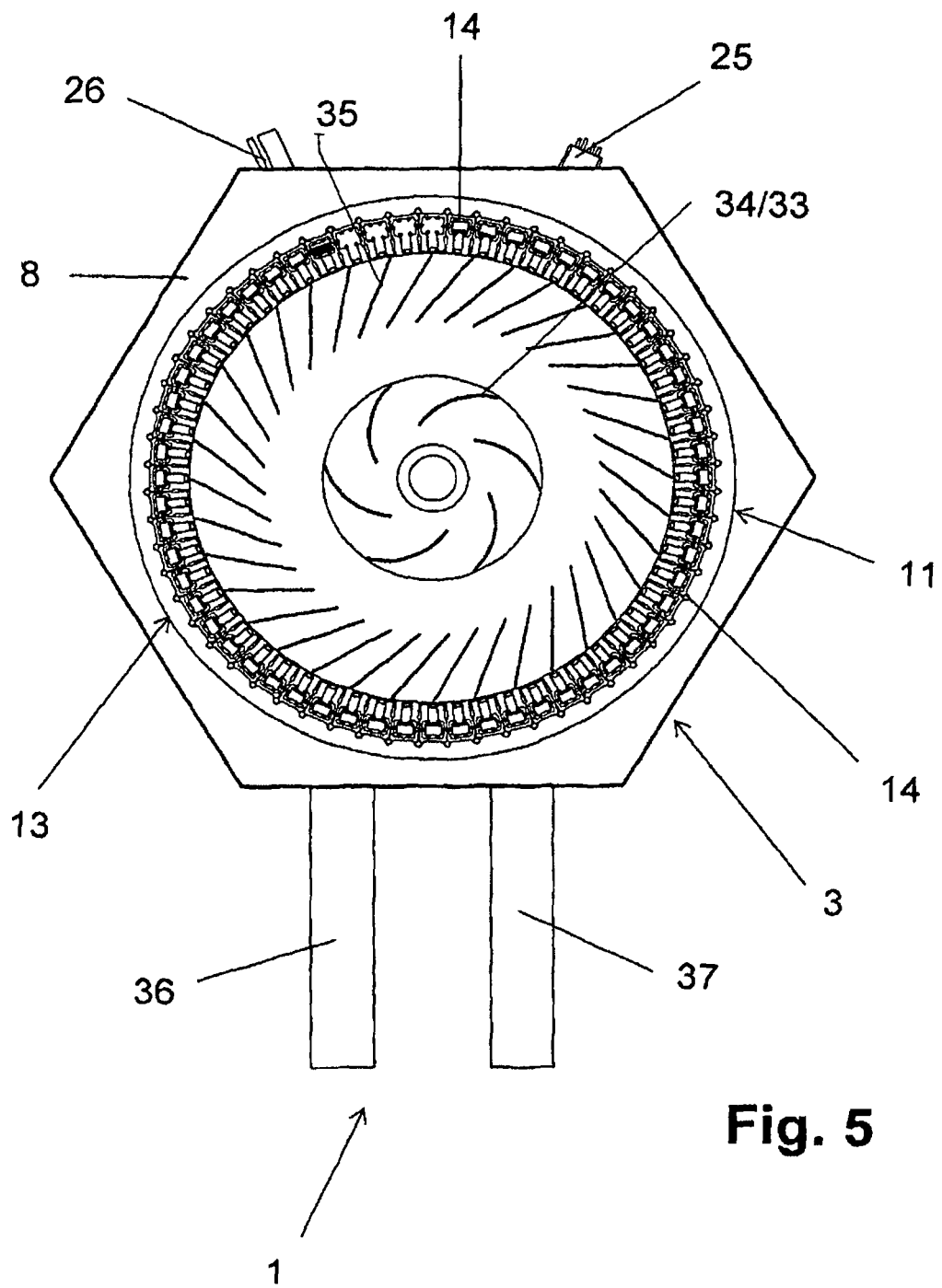
FIG. 5 is a simplified depiction of a horizontal section through an upper treatment zone serving as a pre-heating zone of the device in FIG. 1.

The device designated generally in the figures as 1 serves to sterilize closures 2, for example closures in the form of caps, screw caps, flat caps or crown corks etc., that are used to close containers not shown, e.g. in the form of bottles. The device 1 for this preferably forms an assembly that is connected before a closing machine for closing the containers and from which the sterilized closures 2 are supplied to the closing machine under sterile or germfree conditions.

The device 1 comprises, among other things, a device housing 3 that, in top view, has a polygonal shape enclosing a vertical machine axis MA. In the embodiment shown, the housing is hexagonal. The interior of the housing 3, with the exception of inlets and outlets for the closures 2, is tightly sealed against the environment.

In the embodiment shown, the housing 3 comprises three successive housing segments in the axial direction of the machine axis MA, namely: an upper housing segment 3.1, which substantially comprises the upper hexagonal housing wall 5 fitted with an inspection cover 4, a peripheral wall 6, which is fitted with large format inspection windows 7 each tightly closed by glazing, and an intermediate floor 8, an adjacent housing segment 3.2 with a closed peripheral wall 9, and an adjacent housing segment 3.3, which substantially comprises the lower hexagonal housing wall 10 and peripheral wall 6 with the large format inspection windows 7 tightly closed by glazing.

This gives a modular structure, which is simple to manufacture, of at least the housing 3.

The intermediate floor 8 divides the interior of the housing 3 into an upper treatment zone 11, formed in housing segment 3.1 and a lower treatment zone 12, separate from treatment zone 11 and formed in housing segments 3.2 and 3.3. In both treatment zones 11 and 12, a rotor 13 is provided that can be driven to circulate about the common vertical machine axis MA. In the embodiment shown, the two rotors 13, which are each part of a transport system for the closures 2, are designed to be identical, each as a circular cylindrical hollow drum with a drum casing with a cage-like structure that is formed by a multiplicity of closure holders 14, each receiving a multiplicity of closures 2. The closure holders 14, which are oriented with their longitudinal extension to be parallel or substantially parallel to machine axis MA are, at their upper end, open for introduction of closures 2 and are, at their lower end, open for discharge of closures 2. The closures, as a whole, form the cage-like structure or casing of the respective rotor 13 and are here arranged distributed on the periphery of rotor 13 at constant angle or pitch intervals about the machine axis MA. Ring-like brackets 15 concentrically surrounding the machine axis MA and offset to each other in the direction of this axis connect the closure holders 14 together and to the grid-like structure of the respective rotor 13. In the region of their lower ends, the closure holders 14 of each rotor 13 are attached to a circular disc-shaped carrier element 16 arranged coaxial with machine axis MA such that the closure holders 14 each protrude beyond the peripheral surface of the carrier element 16.

The closure holders 14 are also formed into a grid. Each consists of several rod or bar-like closure guide rails spaced from each other and oriented parallel to machine axis MA. The guide rails for between them a receiving chamber to receive a multiplicity of closures 2 such that the closures 2 in each closure holder 14 form a single row extending in an axial direction parallel to machine axis MA and exposed as far as possible in the closure holders 14, i.e. each is covered only on a small part of its surface by the closure guide rails 14. Furthermore the closure holders 14 in the embodiment shown are designed such that the closures 2 in the closure holders 14 have a pre-specified orientation in relation to the machine axis MA, such that they are oriented with their closure or cap axis radial to the machine axis MA and, for example, with their open cap side radially outwards.

With the carrier element 16 or with a shaft 17 connected with the carrier element 16 and arranged coaxial with machine axis MA, the upper rotor 13 in the treatment zone 11 is mounted in a bearing 18 of the intermediate floor 8 and the lower rotor 13 in the treatment zone 12 is mounted on a bearing 19 provided on the lower housing wall 10, both of which are rotatable about machine axis MA. An independent drive with gears and an independent drive motor (electric motor) is allocated to each rotor 13, namely drive 20 to the upper rotor 13 and drive 21 to the lower rotor 13.

In the upper region of treatment zone 11, above the movement track of the closure holders 14, there is provided a closure pickup 22 to which the closures 2 to be sterilized are supplied via a delivery section 23 in which the closures 2 already have the orientation corresponding to their orientation in the closure holders 14. In the region of the underside of housing 3, below the movement track of the closure holders 14, there is a closure discharge that is substantially formed by the inlet or open end of a delivery section 24 that extends with this end through the lower housing wall 10 into the lower treatment zone 12 and with its open end is arranged below the movement track of the closure holders 14 of the lower rotor 13. Above the delivery track 24, the sterilized closures 2 are supplied germ-free to the closing machine, which is not shown.

In addition to the closure discharge formed by the delivery section 24, two additional closure discharges are provided, which are each formed by a closure guide 25 and 26, for empty running of the device 1 and/or rotors 13 i.e. for removal of closures 2 from the device 1 and/or from the rotors 13 or their closure holders 14, for example in the event of fault in a plant containing the device 1, on a format change i.e. on changeover from one closure type to another closure type etc. The closure guides 25 and 26 guided out of the housing 3 each terminate in the treatment zones 11 and 12 respectively below the movement track of the closure holders 14. By corresponding control means not shown, the inlets there of the closure guides 25 and 26 can be controlled such that closures 2 do not reach the closure guides 24 and 26 in normal operation of the device 1 but only on empty running of the device 1 and/or rotors 13.

In the embodiment shown, the delivery sections 23 and 24 and the closure guides 25 and 26 are each formed by several guide rails receiving and guiding the closures between them. Furthermore, in the embodiment shown, at least the delivery sections 23 and 24, at least in the vicinity of the device 1, each have a vertical course so that the closures 2 in these delivery sections, as in the closure holders 14, are moved or conveyed purely by gravity. In order to avoid recontamination of the sterilized closures 2 on delivery section 24, this is held in a sheath or housing, which is not shown, that is preferably exposed to a positive pressure of a sterile gaseous and/or vaporous medium, for example with pressurized sterile air.

In the inside of housing 3, between the underside of the upper rotor 13 and the top of the lower rotor 13, there is formed a treatment section or zone 27 comprising a grid-like closure guide 28 that extends parallel to machine axis MA and is designed to receive a multiplicity of closures 2 in a single row, and in which the closures 2 are oriented in the same manner in relation to machine axis MA as in the closure holders 14. The closure guide 28 passing through the intermediate floor 8 is arranged with its upper open end at a closure delivery position 29 below the movement track of the closure holders 14 of the upper rotor 13 and with its lower open end at a closure delivery position 30 above the movement track of the closure holders 14 of the lower rotor 13. The closure guide 28, at least over the majority of its length, is held in a chamber 31 that is located below the intermediate floor 8 in the treatment zone 12 and in which the closures 2 are treated with or exposed to the hot sterilizing agent that is formed by $H_2O_2$ vapor or contains $H_2O_2$ vapor in a gaseous and/or vaporous carrier medium and is introduced into chamber 31 via an inlet 32.

The upper treatment zone 11 serves to preheat the closures 2 to a desired or preselected preheat temperature, for example in the range between 50° C. and 85° C. For this, within the rotor 13 there is provided a heater 33 with a circulating or blown air fan 34 that has a multiplicity of blade-like guide vanes or impellers 35 and that is driven such that within the treatment zone 11 there is a flow of hot gaseous and/or vaporous medium, for example a hot air flow, with a flow direction from the circulating air fan 34 through the rotor 34 or through the closure holders 14 radially towards the outside (mainly in the lower region of treatment zone 11) and then again at least partly through the rotor 13 or through the closure holders 14 back in the direction of the rotor center (mainly in the upper region of the treatment zone 11).

The lower treatment zone 12 serves substantially to dry the closures 2 with a sterile, preferably heated, gaseous and/or vaporous medium, for example with preferably heated sterile air. The gaseous and/or vaporous medium is supplied via an inlet 36 and extracted via an outlet 37. The design is such that there can be no direct flow between the inlet 36 and outlet 37, and that, via openings in the intermediate floor 8, a flow of sterile medium is established from the treatment zone 12 into the treatment zone 11, and, at the passages at least of the delivery section 23 and the closure guides 25 and 26, a flow of sterile medium is established towards the outside in order to prevent the penetration of ambient air into the interior of the housing 3.

The closure pickup 22 and the delivery position 29 are arranged at an angular distance that corresponds to a multiple of the pitch interval of the closure holders 14 on the upper rotor 13 such that whenever a closure holder 14 of the upper rotor 13 with its upper open end has reached the closure delivery point 22, another closure holder 14 of this rotor with its lower open end is at the delivery position 29. In the same way the lower delivery position 30 and the closure discharge formed by delivery section 24 are spaced at an angular interval that corresponds to a multiple of the pitch spacing of the closure holders 14 on the lower rotor 13 such that whenever a closure holder 14 of the lower rotor 13 with its upper open end has reached the delivery position 30, another closure holder 14 of this rotor with its open end is at the closure discharge.

In relation to the direction of rotation of the rotor 13 concerned, the closure pickup 22 and the closure delivery position 29 and the closure delivery position 30 and the closure discharge formed by the delivery section 24 are spaced from each other by as large an angular region as possible, for example by an angular region of at least 330°.

At least during normal operation, the two rotors 13 are driven by their drives 20 and 21 in the same direction and in synchrony such that, in particular when a closure holder 14 of the upper rotor 13 is at the delivery position 29, an empty closure holder 14 of the lower rotor is ready at the delivery position 30.

At the closure pickup 22, in each stoppage phase of the cycled rotary movement of the upper rotor 13, a closure holder 14 of this rotor is filled, for example, completely with closures 2 that are provided in delivery section 23 as a sufficiently large stock of closures. With the circulating upper rotor 13, the closures 2 held in the respective closure holder 14 are then moved from the closure pickup 22, through the treatment zone 11, to the closure delivery position 29 and there heated by the hot flow generated by the heater 33 and the circulating air fan 34.

Figure 6:
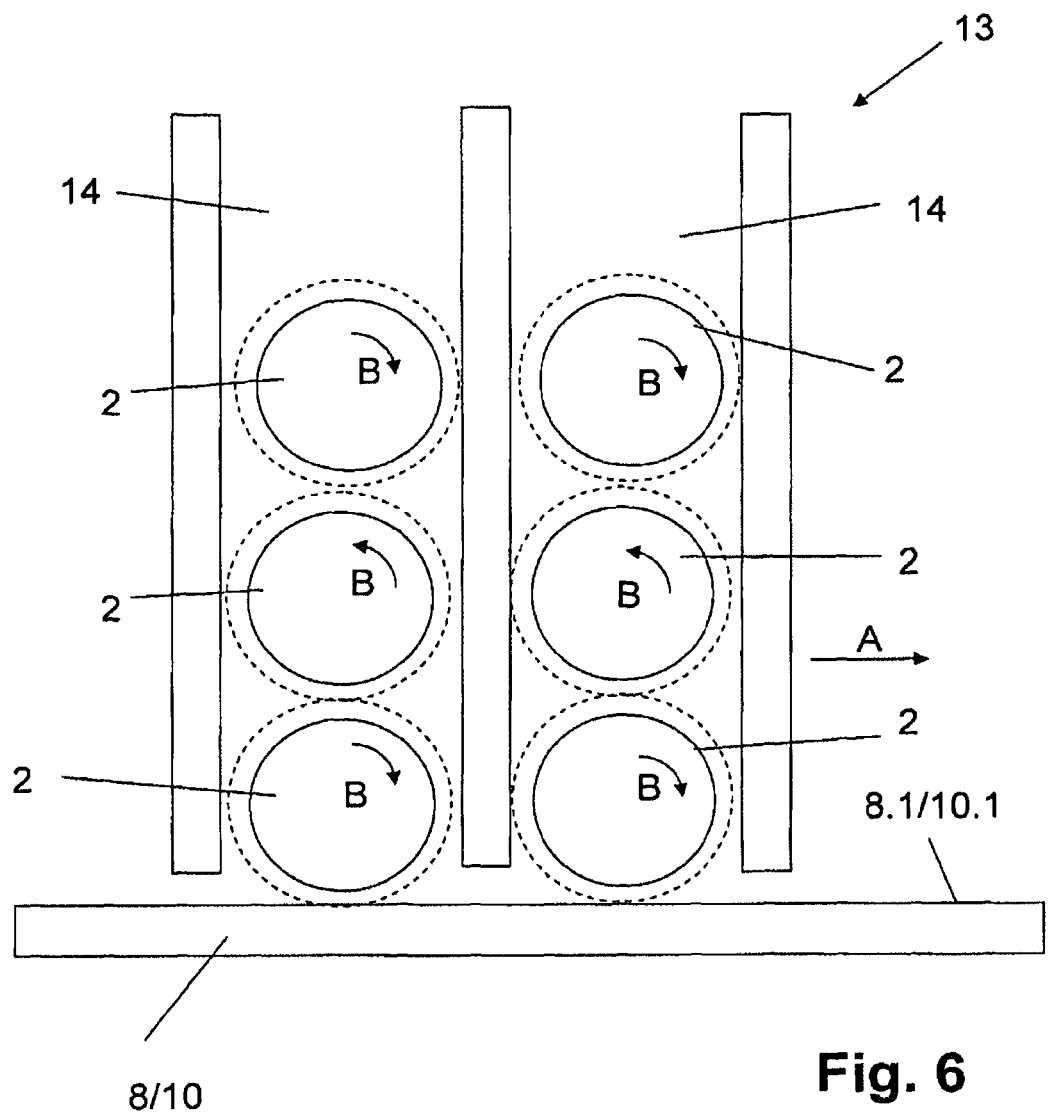
FIG. 6 is a simplified partial depiction and side view, of two of the closure holders formed on a rotor of the device.

As shown in FIG. 6, on the rotary movement of rotor 13 indicated with arrow A, the lowest closure 2 of each closure holder 14 that is arranged in a closure holder 14, rolls with its peripheral surface in the manner of a friction wheel on a closure contact surface 8.1 formed by the intermediate floor 8 and not carried with rotor 13, whereby according to arrow B a rotary or rolling movement is generated for the lowest closure 2 and is transmitted from closure to closure to all closures 2 arranged in the respective closure holder 14 and lying against each other with their peripheral surfaces so that all closures 2 in each closure holder 14 rotate in opposite directions according to arrow B and are thus exposed to the hot air flow over their entire surface.

Whenever a closure holder 14 of the upper rotor 13 has reached the closure delivery position 29, all closures 2 of that holder fall through the treatment zone 27 or through the closure guide 28 there into a ready, empty closure holder 14 of the lower rotor 13. In the treatment zone 27, the closures 2 are exposed to the hot sterilizing agent, which is constantly supplied via a connection 32.

The closures 2 held in the respective closure holder 14 of the lower rotor 13 are moved with this rotor 13 through the treatment zone 12 and there dried by the flow sterile gaseous and/or vaporous medium. According to FIG. 6, again on the rotary movement (arrow A) of the lower rotor 13, the lowest closure in each closure holder 14 rolls with its peripheral surface in the manner of a friction wheel on a closure contact surface 10.1 formed by the housing wall 10 and not carried with the rotor 13, generating a rotary or rolling movement (arrow B) which is transferred from closure to closure to all closures 2 arranged in the respective closure holder 14 and lying against each other with their peripheral surfaces so that these rotate in opposite directions (arrow B) and are thus dried optimally on all surface regions. At the closure discharge then all closures fall from the respective closure holder into the delivery section 24 for further delivery to the closing machine.

The separate drives 20 and 21 allow various operating modes of the device 1. Thus for example it is possible at the start of operation to fill the closure holders 14 of the upper rotor completely with closures 2 and then drive the lower rotor 13 via its drive 21 initially in cycles when a closure row is introduced from the upper rotor 13 into the closure holder 14 of the lower rotor 13. Conversely before the end of operation it is also possible to switch off the upper rotor 13 and run the lower rotor empty with delivery of all closures to the delivery section 24. Furthermore the separate drives 20 21 create the possibility, for example on fault and/or on a format change, of running the rotors 13 empty individually, i.e. delivering the closures for example also via the closure guides 25 and 26.

The invention has been described above with reference to one embodiment example. Evidently numerous modifications and derivations are possible without leaving the inventive concept fundamental to the invention.

It has been assumed above that the movement of the closures 2 within the delivery sections 23 and 24, closure guides 24 and 26, the closure guide and closure holders 14, takes place by gravity. In principle it is also possible to provide, at these elements, transport nozzles for the emergence of a sterile gaseous and/or vaporous transport medium, for example for the emergence of sterile transport air.

Furthermore, at the treatment zones 11 and 12 and at the treatment section 27, preferably means not shown are provided for cleaning, and/or measurement sensors not shown are provided for measurement and/or monitoring of the state of the treatment zones.

Furthermore, the treatment zone 27 can also comprise at least two preferably parallel closure guides 28, which are then arranged so that in each stoppage phase of the cycled rotary motion of the rotors 13, each closure guide 28, with its inlet or with its upper end, lies opposite the outlet or the lower open end of a closure holder 14 of the upper rotor 13, and with its outlet or its lower end opposite the inlet or open upper end of an empty closure holder 14 of the lower rotor 13. The closure pickup 22 and the closure discharge formed by the delivery section 24 are then designed for simultaneous filling and evacuation of several closure holders 14.

Furthermore the respective closure contact surfaces 8.1 and/or closure contact surface 10.1 can also be formed such that they are moved relative to rotor 13 or circulate about the machine axis MA so as to achieve the above-mentioned rolling movement of the lowest closures 2 respectively and hence the opposite movement of the closures 2 in the closure holders 14.

LIST OF REFERENCE NUMERALS

1 Device
2 Closure
3 Housing
3.1-3.3 Housing segment
4 Inspection cover
5 Upper housing wall
6 Housing wall
7 Inspection window
8 Intermediate floor
8.1 Closure contact surface
9 Housing wall
10 Lower housing wall
10.1 Closure contact surface
11,12 Treatment zone
13 Rotor
14 Closure holder
15 Bracket
16 Carrier element
17 Shaft
18, 19 Bearing
20, 21 Drive
22 Closure pickup
23, 24 Delivery section
25, 26 Closure guide 27 Treatment section
28 Closure guide
29, 30 Delivery position
31 Chamber of treatment section 27
32 Inlet for sterilizing agent
33 Heater
34 Circulating air fan
35 Air guide plate
36 Sterile air inlet
37 Sterile air outlet
A Rotary movement of rotor 13
B Rolling or rotary movement of closures 2
MA Vertical machine axis

The invention claimed is:

1. An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, wherein at least one of said rotors is formed as a hollow drum with a cage-like drum casing formed by a multiplicity of closure holders.

2. The apparatus of claim 1, further comprising a device for generating a flow of hot gaseous medium to heat said closures.

3. The apparatus of claim 2, wherein said device comprises a heating device.

4. The apparatus of claim 3, wherein said device further comprises a fan.

5. An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, wherein said multiplicity of closure holders comprises a cage-like holder with guide rails extending along a longitudinal direction thereof between which a closure is held.

6. The apparatus of claim 5, wherein said guide rails are rods.

7. The apparatus of claim 5, wherein said guide rails are bars.

8. The apparatus of claim 5, wherein said rotors are oriented such that said rotor axes of said rotors are coaxial to each other.

9. The apparatus of An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, wherein said rotors are oriented such that said rotor axes of said rotors are coaxial to each other.

10. The apparatus of claim 9, further comprising a device housing in which said treatment zones are formed, a housing wall separating the environment from at least one of said first treatment zone and said third treatment zone, a large area inspection window fitted to said housing wall, and glazing for tightly closing said inspection window.

11. The apparatus of claim 9, further comprising at least one drive for stepped or cycled driving of said rotors.

12. An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, wherein said closure holder is oriented with longitudinal extensions thereof in a direction parallel to rotor axes thereof.

13. The apparatus of claim 12, wherein said rotors are oriented such that said rotor axes of said rotors are in a vertical direction.

14. An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, further comprising an independent drive for each rotor.

15. The apparatus of claim 14, wherein said second treatment zone is formed on a transport section extending between one of said first delivery position and said second delivery position and said first delivery position and a guide for said closures.

16. The apparatus of claim 14, further comprising a device for generating a flow of hot gaseous medium to heat said closures.

17. An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, further comprising additional controllable closure outlets for removing closures from at least one of said first treatment zone, said third treatment zone, closure holders of a rotor in said first treatment zone, and closure holders of a rotor in said third treatment zone, said additional controllable outlets being configured for application of a positive pressure to at least one of said first treatment zone and said third treatment zone.

18. The apparatus of claim 17, further comprising at least one drive for stepped or cycled driving of said rotors.

19. The apparatus of claim 17, further comprising an independent drive for each rotor.

20. An apparatus for sterilizing cap-like closures for containers, said apparatus comprising a transport system for moving said closures through at least three treatment zones, said at least three treatment zones comprising a first treatment zone in which said closures are preheated, a second treatment zone in which said closures are exposed to a sterilizing agent, and a third treatment zone in which said closures are at least one of activated and dried in a drying medium selected from a group consisting of a sterile gaseous medium, a vaporous medium, and sterile air, wherein said first and third treatment zones each comprise a rotor that can be driven to circulate about a rotor axis thereof, and a multiplicity of closure holders formed on a periphery of each of said rotors for moving closures through said first treatment zone from a closure pickup disposed therein to a first closure delivery position, and through said third treatment zone from a second closure delivery position disposed therein to a closure discharge, and wherein said second treatment zone is disposed between said first and second closure delivery positions such that closures delivered to said first closure delivery position, after passing said second treatment zone and after exposure to said sterilizing agent, are passed on to a closure holder ready at said second closure delivery position of said rotor in said third treatment zone, further comprising a closure contact surface disposed at an open lower end of a closure holder, said contact surface being immovable with said rotor and movable relative to said rotor, wherein a closure adjacent to said closure contact surface rolls on circulation of said rotor to generate a closure rotary movement transferred from closure to closure in said closure holder.

21. The apparatus of claim 20, wherein said third treatment zone comprises an inlet and an outlet for said drying medium.

* * * * *